(12) United States Patent
Markart

(10) Patent No.: US 6,200,442 B1
(45) Date of Patent: Mar. 13, 2001

(54) MEASURING DEVICE FOR THE ELECTRICAL MEASUREMENT OF TEST STRIPS

(75) Inventor: Ernst Markart, Munich (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

(21) Appl. No.: 09/218,326

(22) Filed: Dec. 22, 1998

(30) Foreign Application Priority Data

Aug. 20, 1998 (DE) .............................................. 298 14 996

(51) Int. Cl.$^7$ ..................................................... G01N 27/26
(52) U.S. Cl. ........................ 204/400; 422/82.01; 324/450; 204/403
(58) Field of Search ........................ 204/400; 422/82.01; 324/446, 450

(56) References Cited

U.S. PATENT DOCUMENTS 5,821,399 * 10/1998 Zelin ..................................... 73/1.02

* cited by examiner

Primary Examiner—T. Tung
(74) Attorney, Agent, or Firm—McCormick, Paulding & Huber LLP

(57) ABSTRACT

In a measuring device for measuring the concentration of a substance in a liquid applied to the test field of a test strip having two first electrical contacts at its forward end connected to the test field, a conductor plate inside of the device carries a measuring and evaluation circuit and also has formed on it two second electrical contacts which two second electrical contacts, when the forward end of the test strip is inserted into the device through an insertion slot, are brought into contact with the two first contacts on the test strip to connect the test field of the test strip in circuit with the measuring and evaluation circuit of the conductor plate.

17 Claims, 3 Drawing Sheets

MEASURING DEVICE FOR THE ELECTRICAL MEASUREMENT OF TEST STRIPS

FIELD OF THE INVENTION

The invention concerns a measuring device for the electrical measurement of test strips for determining the concentration of substances in a liquid, wherein each test strip has a test field to be wetted with the fluid under investigation, from which test field two electrodes lead to first contact elements on the test strip, the measuring device having a test strip receiver in which are arranged second contact elements for contacting the first contact elements, which second contact elements are connected with a measuring and evaluation circuit of the measuring device.

BACKGROUND OF THE INVENTION

The second contact elements of customary measuring devices are usually formed by spring contact elements arranged in a plug portion. With this there arise high work tool costs for the manufacturing of the contacts and of the plug portion, part costs and assembly costs. Moreover, the spring contact elements are susceptible to wear and damage in the use of the measuring device.

The invention therefore has as its object the provision of a measuring device of the above-mentioned kind in which in simple and economical ways a reliable contact can be made between the contact elements on the test strip and the measuring, and evaluation circuit of the measuring device.

SUMMARY OF THE INVENTION

This object is solved in accordance with the invention in that the second contact elements are formed from contact paths formed on a conductor plate of the measuring device carrying the measuring and evaluation circuit.

In the inventive solution, the previously needed plug portion, including the contact springs, is avoided. On the already previously provided conductor plate, the conductor paths, which previously made the contact to the contract springs of the plug portion, are formed as contact paths. This can take place in the same work procedure as the manufacturing of the conductor plate.

The contact paths guarantee, on one hand, a large surfaced secure contact with the contact elements on the test strip and, on the other hand, they are only slightly susceptible to wear or damage. Above all, they cannot be bent during the insertion of the test strip as was often the case with previous spring contact elements.

The contact paths can pass around the front end of the conductor plate facing the insertion opening of the test strip receiver, so that an early and secure contact between the contact paths on the conductor plate and the contact elements of the test strip can be made. To make the contact effect still more secure, contact points forming raised bumps on the contact paths can be provided. For the same reason, the section of the conductor plate carrying the contact paths can be relieved to form spring arms. The elasticity of the conductor plate material can also be so chosen so that the contact paths are pressed against the contact elements of the test strip with a given pressure.

Another possibility for making a secure contact between the contact elements of the test strip and the contact paths of the conductor plate exists in that the test strip receiver opposite to the contact path carrying conductor plate is provided with a pressure piece for pressing the test strip onto the contact paths. This pressure piece can be loosely inserted in the measuring device so that it can be removed for cleaning of the test strip receiver. In order that the pressure piece is securely held in the measuring device, it can be made snappable into the measuring device.

The pressure piece can also be so formed that, because of an inherent elasticity, it creates the pressing pressure. However, at least one spring element can also be provided to bias the pressure piece in the direction toward the conductor plate.

Preferably, the pressure piece has guide elements for the test strip, and an abutment can also be provided on the pressure piece for limiting the insertion path of the test strip in the insertion direction.

In a plate shaped formation of the pressure piece, it advantageously has a projection for engagement with the test strip in order to achieve secure pressing of the test strip against the contact paths of the conductor plate.

By means of the pressure piece, the test strip in the test strip receiver is held by a clamping effect, and preferably the pressure piece is shiftable out of the pressing position in order to free the test strip. It is then, for example, sufficient to shift the pressure piece and to let the test strip fall out of the test strip receiver without the test strip having to be touched again.

On the conductor plate near the contact paths, but outside of the insertion path of the test strip, a third contact element connected with the measuring and evaluation circuit can further be provided on the conductor plate, which third contact element is intended to make a data connection to a data processing device, such as, for example, a personal computer, for example, over a conducting element insertable into the test strip receiver, with the help of which data processing device the measured results can be read out of the measuring device and processed.

Since the test strips frequently are dipped into the liquid to be investigated and thereby deploy a relatively large amount of moisture, it is advantageous if the test strip receiver is sealed by a fluid tight cover from the remainder of the measuring device.

Further features and advantages of the invention will be apparent from the following description which in connection with the accompanying drawings explain the invention by way of an exemplary embodiment.

DESCRIPTION OF THE PREFERRED EMBODIMENTS

Figure 1:
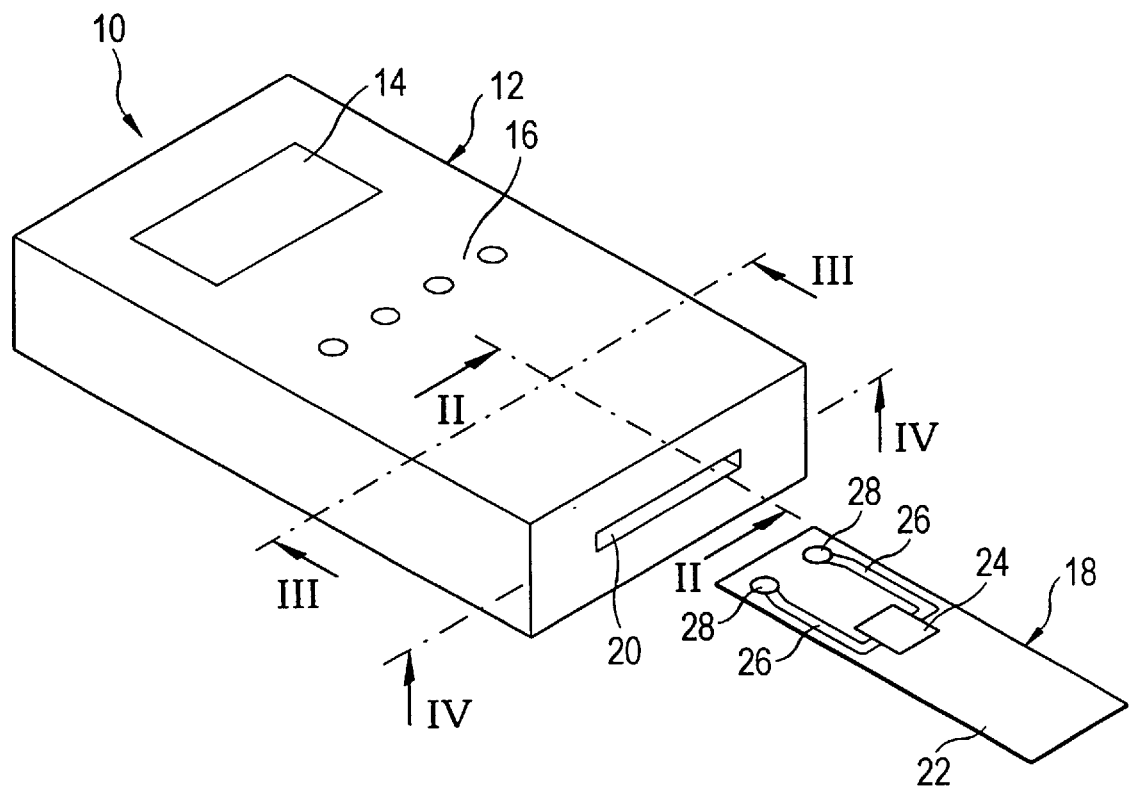
FIG. 1—a schematic perspective view of a measuring device for the electrical measurement of a test strip.

FIG. 1 shows a measuring device, indicated generally at 10, with a housing 12, an indicator device 14, and an operating field 16. The measuring device 10 serves to receive a test strip 18 which is insertable into a test strip receiver inside the measuring device 10 through an insertion slot 20 in the housing 12.

The test strip 18 has, in a way known in itself, a carrier 22 with a test field 24 from which two electrodes 26 extend to first contact elements 22 near the left end of the carrier 22 as seen in FIG. 1. If a liquid to be investigated is applied to the test field 24, with the help of the measuring device in a way known in itself electrical values in the test field 24 can be obtained through the first contact elements 28 and the electrodes 26, from which values conclusions about the concentration of certain substances in the investigated liquid can be drawn. The position of the test strip inside of the measuring device 10 and the electrical connection of the first contact elements with the measuring and evaluation circuits inside of the measuring device 10 will now be described in closer detail in connection with FIGS. 2–5.

Figure 2:
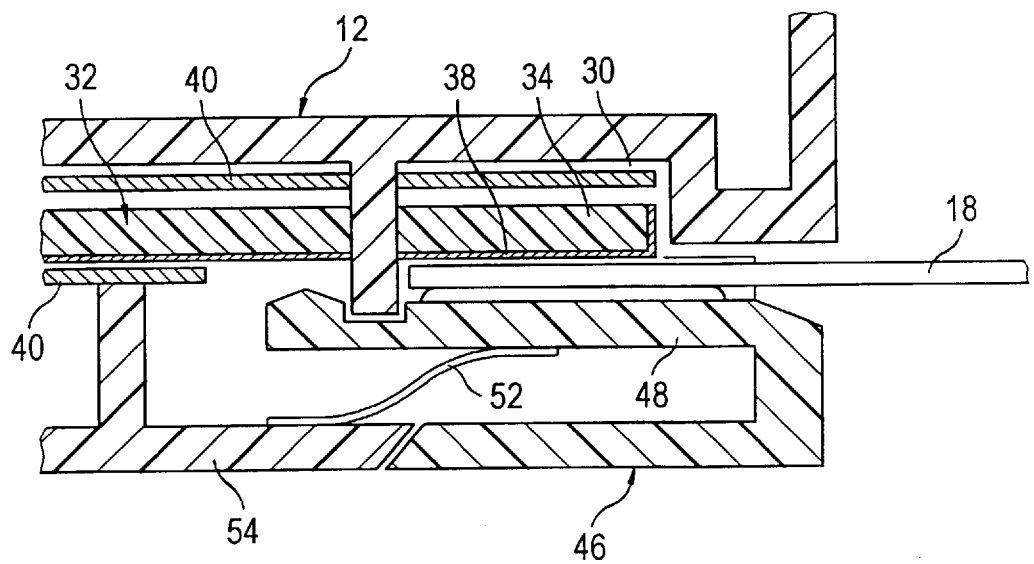
FIG. 2—a schematic partial section through the measuring device along the line II—II of FIG. 1.
Figure 3:
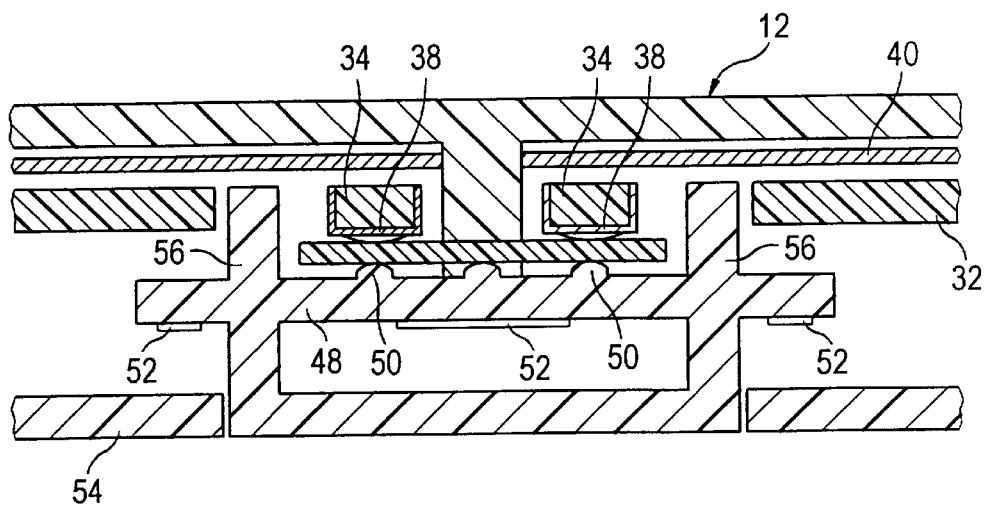
FIG. 3—a schematic partial section through the measuring device along the line III—III of FIG. 1.
Figure 4:
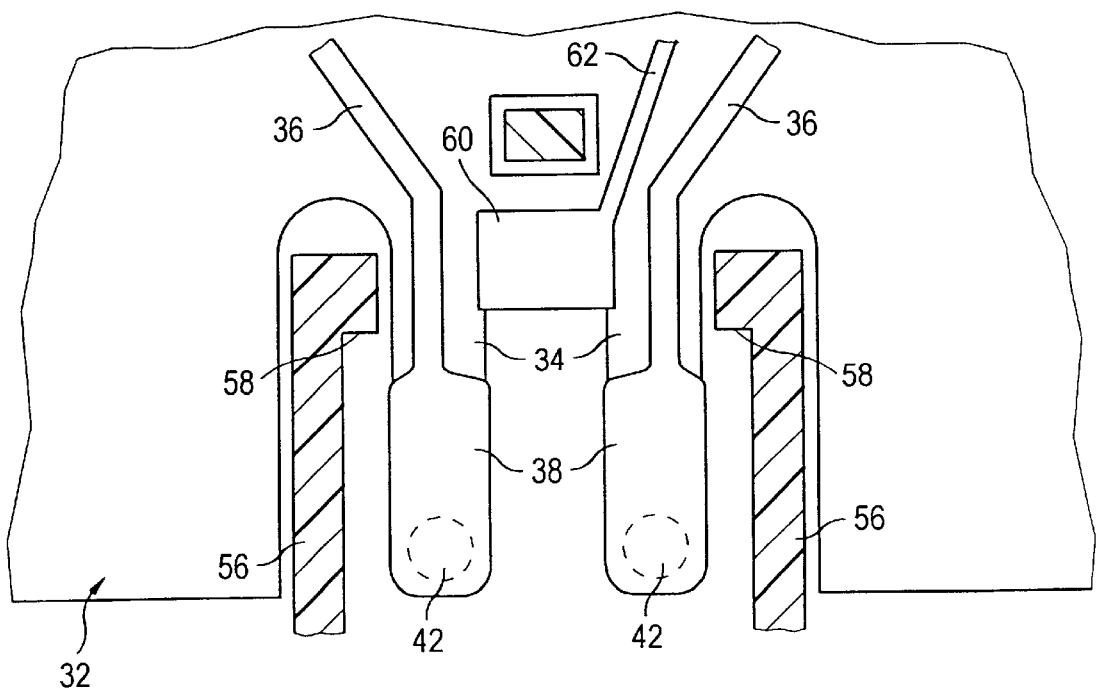
FIG. 4—a schematic partial sectional view through the measuring device of the invention and the insertion plane of the test strip along the line IV—IV of FIG. 1.

Inside of the housing 10 is provided a test strip receiver 30 following the insertion slot 20. Into this test strip receiver 30 extends a conductor plate 32 arranged inside the housing 10, which conductor plate carries the non-illustrated measuring and evaluating circuit of the measuring device 10, and has two freely separated tongue-like conductor plate sections of 34 (FIG. 4). On the tongues 34 are conductor paths 36 which near the free ends of the tongues 34 are widened to contact paths 38 entirely covering the tongues 34. These contact paths 38, which in FIG. 4 are seen from below, are bent around the forward ends of the tongues 34 (FIG. 2) and are so arranged that they can come into electrical contact with the first contact elements 28 of the test strip 18 when the test strip 18 is inserted into the test strip receiver 30 as seen in FIG. 2. The conductor plate 32 as seen in FIG. 2 is isolated from the remaining portion of the measuring device 10 by liquid tight sealing elements 40.

Figure 5:
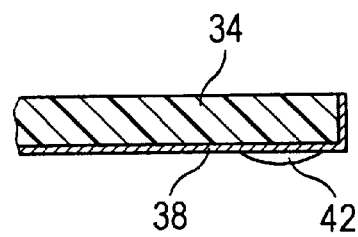
FIG. 5—a partial longitudinal section through a contact path carrying conductor plate section.

To assure a secure contact between the contact paths 38 and contact elements 28 on the test strip 18 different measures are provided. For one, small bumps are formed on the contact paths 38 to provide contact points 32 (FIGS. 4, 5). As another, a pressure piece indicated generally at 46 is provided which limits the test strip receiver 30 from below by a plate shaped section 48. The plate shaped section 48 has on its side facing the conductor plate 32 ribs 50 arranged opposite to the contact paths 38 to support the contact strip 18 exactly below the contact paths 38. This entire pressure piece 36 is inserted releasably in the housing 12 of the measuring device 10 and is biased in the direction toward the conductor plate 32 by leaf spring elements 52 supported on the bottom 54 of the housing 12. Thereby, the test strip 18 with its contact elements 28 is reliably pressed against the contact paths 38 and the contact points 42.

To exactly determine the position of the test strip 18 in the test strip receiver 30 and to make certain that the contact elements 28 come into contact with the contact points 42 the pressure piece 46 has lateral guide bars 56 which at their inner ends with respect to the device inner space have matching end abutments 58 (FIG. 4). In a modified embodiment, these guide bars are not on the pressure piece 46 but are arranged on the device housing 12, for example, on the housing wall 44 (FIG. 3) covering the upper portion of the test strip receiver 30.

Between the two contact paths 38, but outside of the insertion area for the test strip 18, delimited by the end abutments 58, is further a third contact element 60 which is connectable with the measuring and evaluation circuit through a conductor path 62 and which serves through a conductor element inserted into the test strip 30 receiver in place of the test strip, to make a data connection between the measuring and evaluation circuit of the measuring device 10 and a personal computer.

When no test strip is positioned in the test strip receiver, it can be advantageous to short-circuit the contact paths 38. This can be accomplished for example by a conductor bridge running perpendicularly over the ribs 50 of the pressure piece 46 or by a metal layer on the pressure surface of the pressure piece 48 facing the contact paths.

Figure 6:
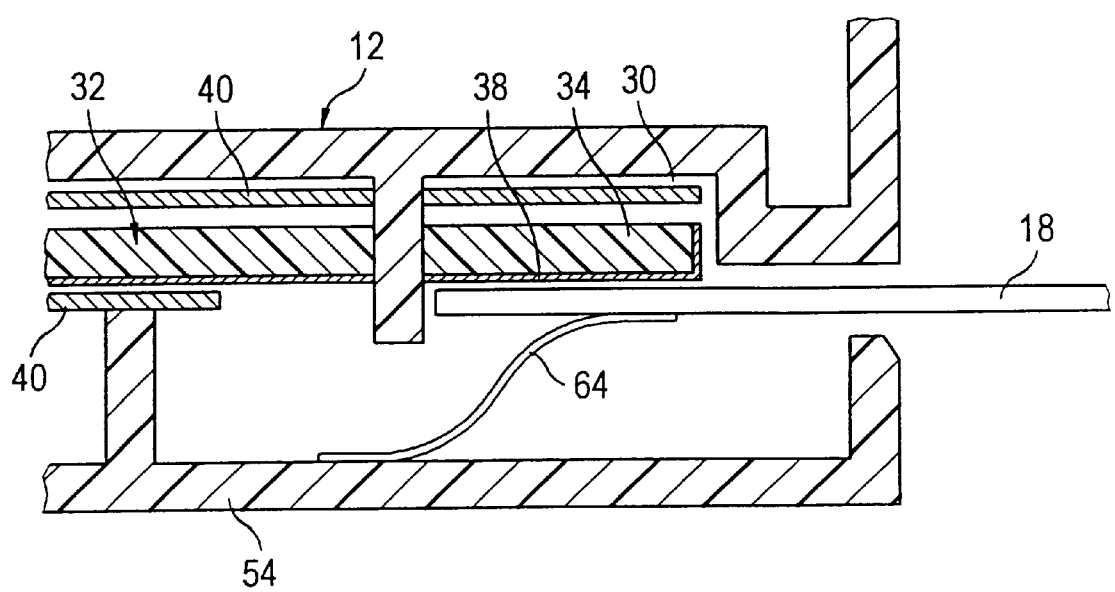
FIG. 6—a schematic partial section view corresponding to FIG. 2 through a modified embodiment of the invention.

In an alternate embodiment illustrated in FIG. 6, the pressure piece is formed by a leaf spring 64 which presses the test strip 18 against the contact paths, and in the absence of a test strip, bridges the contact paths 38.

What is claimed is:

1. A measuring device for electrically measuring test strips (18) for determining the concentration of substances in liquids with each test strip (18) having a test field (24) to be moistened by a liquid to be investigated, from which test field two electrodes (26) lead to first contact elements (28) on the test strip, the measuring device (10) having a test strip receiver (30) in which are arranged two second contact elements (42) for contacting the first contact elements (28), which two second contact elements are connected with a measuring and evaluation circuit of the measuring device (10), characterized in that the two second contact elements are formed respectively by two contact paths (38) on a conductor plate (32) located in the measuring device (10) and carrying the measuring and evaluation circuits the conductor plate (32) having a first surface facing the two electrodes (26) of a test strip (18) when the test strip is received in the test strip receiver (30) and the contact paths (38) which form the second contact elements being in engagement with and fixed to the first surface of the conductor plate so that the second contact elements are not movable, resiliently or otherwise, relative to the conductor plate.

2. A measuring device, according to claim 1, further characterized in that the two contact paths (38) extend around the forward end of the conductor plate (32) which forward end is directed toward the insertion opening (20) of the test strip receiver (30).

3. A measuring device, according to claim 1, further characterized in that on the two contact paths (38) bumps are provided which form the two second contact elements (42).

4. A measuring device, according to claim 1, further characterized in that a section of the conductor plate (32) carrying the two contact paths (38) is cutaway to form two spring arms (34) each carrying a respective one of the control paths.

5. A measuring device, according to claim 1, further characterized in that in the area of the test strip receiver (30) opposite to the contact path (38) carrying conductor plate (32) a pressure piece (46) is provided for pressing the test strip (18) onto the contact elements (42).

6. A measuring device, according to claim 5, further characterized in that the pressure piece (46) is releasably insertable into the measuring device (10).

7. A measuring device, according to claim 6, further characterized in that the pressure piece (46) is snappable into the measuring device (10).

8. A measuring device, according to claim 5, further characterized in that the pressure piece (46) is biased by at least one spring element (52) in the direction toward the conductor plate (32).

9. A measuring device, according to claim 5, further characterized in that the pressure piece (46) has guide elements (56) for the test strip (18).

10. A measuring device, according to claim 5, further characterized in that the pressure piece (56) has an abutment (58) limiting the insertion path of the test strip (18) in the insertion direction.

11. A measuring device, according to claim 5, further characterized in that the pressure piece (46) is plate shaped and has definite projections (50) for supporting the test strip (18).

12. A measuring device, according to claim 5, further characterized in that the pressure piece (46) is shiftable out of the pressing position to release the test strip (18).

13. A measuring device, according to claim 5, further characterized in that the side of the pressure piece (46) facing the conductor plate carries an electrical conducting bridge for short-circuiting the two contact paths to one another when no test strip is inserted in the device.

14. A measuring device, according to claim 5, further characterized in that the pressure piece is formed from a leaf spring extending into the test strip receiver (30), the pressure portion of which has at least an electrical conducting upper surface and is so sized that it short-circuits the two contact paths (38) when no test strip is inserted in the device.

15. A measuring device, according to claim 1, further characterized in that the conductor plate (32) near the conductor paths (38) but outside the insertion path of the test strip (18) is provided with a third contact element (60) connected to the measuring and evaluation circuit.

16. A measuring device, according to claim 1, further characterized in that the test strip receiver (30) is sealed from the remainder of the measuring device by a liquid tight cover (40).

17. A measuring device, according to claim 1, further characterized in that two lateral guide elements (56) for the test strip (18) are located in the test strip receiver (30).

* * * * *

UNITED STATES PATENT AND TRADEMARK OFFICE
CERTIFICATE OF CORRECTION

PATENT NO. : 6,200,442 B1
DATED : March 13, 2001
INVENTOR(S) : Markart

Page 1 of 1

It is certified that error appears in the above-identified patent and that said Letters Patent is hereby corrected as shown below:

<u>Column 4, claim 1,</u>
Line 28, delete "circuits" and substitute -- circuit --.

Signed and Sealed this

Nineteenth Day of March, 2002

Attest:

JAMES E. ROGAN
Director of the United States Patent and Trademark Office

Attesting Officer